US007618792B2

(12) United States Patent
Banerjee

(10) Patent No.: US 7,618,792 B2
(45) Date of Patent: Nov. 17, 2009

(54) MULTIPLEXED DETECTION OF ANTI-RED CELL ALLOANTIBODIES

(75) Inventor: Sukanta Banerjee, Pennington, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 423 days.

(21) Appl. No.: 11/327,589

(22) Filed: Jan. 6, 2006

(65) Prior Publication Data

US 2007/0161056 A1 Jul. 12, 2007

(51) Int. Cl.
*G01N 33/00* (2006.01)
(52) U.S. Cl. .................... 435/7.25; 435/7.21; 435/40.5; 435/373; 436/513; 436/517; 436/519; 436/520; 436/521; 436/546; 436/16; 436/56; 436/172; 436/176; 422/82.05; 422/82.08
(58) Field of Classification Search .............. 435/2, 435/7.21, 7.25, 40.5, 372, 377, 287.2; 436/501, 436/513, 517, 519, 520, 521, 523, 546, 548, 436/10, 16, 17, 56, 64, 164, 172, 176, 1; 422/68.1, 73, 82.05, 820.8
See application file for complete search history.

(56) References Cited

U.S. PATENT DOCUMENTS

| | | | |
|---|---|---|---|
| 4,824,941 A | 4/1989 | Gordon et al. | |
| 5,389,549 A | 2/1995 | Hamaguchi et al. | |
| 5,776,711 A * | 7/1998 | Vyas et al. | ................. 435/7.25 |
| 5,786,219 A * | 7/1998 | Zhang et al. | ................. 436/523 |
| 2004/0137641 A1 | 7/2004 | Holtlund et al. | |

FOREIGN PATENT DOCUMENTS

JP 62-265567 11/1987

OTHER PUBLICATIONS

Liebert M.R. et al: Dynamics of the holes in human erythrocyte membrane ghosts. J.Biological Chemistry 257(19), pp. 11660-11666, (1982).
P.O.Krutzik at al: Fluorescent cell barcoding in flow cytometry allows high-throughput drug screening and signal profiling; Nature Methods, 2006, pp. 361-368, vol. 3 No. 5.
F.Tokumasu et al: Development and application of quantum dots for immunocytochemistry of human erythrocytes; J.Microscopy, 2003, pp. 256-261, vol. 211 pt 3.
P.M.A. De Farias et al: Investigation of red blood cell antigens with highly fluorescent and stable semiconductor quantum dots; J.Bimedical Optics, 2005, pp. 1-4, vol. 10(4).

(Continued)

*Primary Examiner*—Gailene R Gabel
(74) *Attorney, Agent, or Firm*—Eric P. Mirabel

(57) ABSTRACT

Disclosed are methods for detecting antibody in a sample, where the antibody targets an antigen expressed by red blood cells or red blood cell ghosts. Rather than detecting the binding events between a particular antigen antibody pair (as in traditional agglutination based assays) the methods herein allow for multiplexed detection of clinically important allo-immune antibodies to blood group antigens. Specifically the method involves generating fluorescently encoded red blood cells or red blood cell ghosts with known antigen presentation and using them to detect the presence of antibody in serum/plasma with a fluorescent sandwich type immunoassay. The assay results can be read using flow cytometric or fluorescent microscope based imaging techniques.

5 Claims, 10 Drawing Sheets

OTHER PUBLICATIONS

N.Baumgarth et al: A practical approach to multicolor flow cytometry for immunophenotyping; J.Immunological Methods, 2000, pp. 77-97, vol. 243.

F.Cohen et al: Identification of blood group antigens and minor cell populations by the flourescent antibody method; Blood, 1960, pp. 884-900, vol. 15(6).

* cited by examiner (a)

(b)

MULTIPLEXED DETECTION OF ANTI-RED CELL ALLOANTIBODIES

BACKGROUND

Minor blood group antigens (e.g., Jk, Rh, Kell, Kidd and Duffy) can evoke autoantibodies and/or alloantibodies when administered to a sensitized host, causing auto immune hemolytic anemia, hemolytic anemia, hemolytic disease of the newborn and hemolytic transfusion reactions. Sensitization can result from previous transfusions or pregnancy with an antigen-positive fetus. These alloantibodies are ordinarily detected and identified by testing recipient sera, sequentially in separate agglutination assays, against a panel of red blood cells (RBC) of known phenotypes (for example anti-$Jk^a$ antibody can be identified by determining if patient serum will react with $Jk^{a+}$ RBC and not with $Jk^{a-}$ RBC). By selecting multiple samples of RBC of various antigen phenotypes, it is possible to detect the presence or absence of clinically important alloantibodies.

Agglutination assays are conventionally performed in solution, i.e. in a test tube. Interpretation of data for tube agglutination reaction requires skilled and experienced technologists, especially when the reactions are weaker. However, in recent years, newer technologies such as the gel format and coated solid phase format have been developed. The gel technology is based on the principle of controlled agglutination of red cells through a dextran-acrylamide gel [Judd W J, Steiner E A, Knafl P C, Masters C. The gel test: use in the identification of unexpected antibodies to blood group antigens. Immunohematology 1998; 14:59-62]. Microtubes are filled with a mixture of gel, buffer and reagent. At the top of the gel, a mixture of patient serum and various known red cells are added, followed by centrifugation through the gel under controlled conditions. In a negative reaction, the cells pass through the gel and pellet in the bottom of the microtube. Conversely in positive reactions, the red cells are trapped at various levels in the gel, with the strongest reaction (largest agglutinated mass) giving minimal to no observable migration, with most red cells trapped at or near the top of the gel microcolumn. The solid phase system developed by Immucor provides microwells for immobilization of human erythrocytes, and is used in solid phase assays for detection of IgG red cell antibodies to corresponding red cell antigens [Plapp F V, Sinor L T, Rachel J M, et al A solid phase antibody screen. Am J Clin Pathol 1984; 82:179]. Wells are coated with a chemical coupling agent that allows the immobilization of user selected red cells to the microwell surface. Coated wells are incubated with blood products, including sera, plasma or other reagents, under conditions that facilitate antigen-antibody reaction. Following incubation, unbound residual immunoglobins are rinsed from the wells and anti-IgG coated indicator red cells added. Centrifugation brings indicator red cells in contact with antibody bound to the immobilized red cell layer. In case of a positive test, IgG-anti-IgG complexes form between the indicator red cells and the sensitized, immobilized cells. As a consequence of antibody bridging, the indicator cells adhere to the immobilized cells as a second immobilized layer. In the absence of detectable antigen-antibody interactions (negative test), the indicator red cells do not bind to the immobilized cells and pellet to the bottom of the wells as tightly-packed buttons.

The plasma membrane forms the interface between eukaryotic cell interiors and the external environment. Consequently, the functions of proteins embedded in this membrane are varied and include cell-cell and cell-extracellular matrix recognition, reception and transduction of extracellular signals, and the transport of solutes and water molecules into and out of the cell. The heterogeneity of the cell surface protein population often translates into difficulties in development of in-vitro assays using extracted membrane proteins or crude cell lysates. The erythrocyte membrane is a complicated structure consisting of a membrane bilayer, an array of embedded proteins and glycoproteins and a complex layer of cytoskeletal protein network, which is known to be sensitive to external conditions [Steck, T. L. The organization of proteins in the human red blood cell membrane. J. Cell Biol. vol. 62 (1974) 1-19; Byers, T. L. and Branton, D. Visualization of the protein associations in the erythrocyte membrane skeleton. Proc. Natl. Acad. Sci. USA vol. 82 (1985) 6153-6157; Seeman, P., Cheng, D., and Iles, G. H. Structure of membrane holes in osmotic and saponin hemolysis J. Cell. Biol. vol. 56 (1973) 519-527].

Using encoded intact cells as a probe offers an attractive alternative way to screen for ligands that bind to cell surface receptors, and affords development of miniaturized and multiplexed platforms amenable to high-throughput techniques.

Encapsulation of solutes within red blood cells has been widely studied as a means of drug delivery and targeting [Ihler G. M., Glew, R. H. and Schnure, F. W. Enzyme loading of erythrocytes. PNAS vol. 70 (1973) 2663-2666; DeLoach, J. R., Harris, R. L. and Ihler, G. M. An erythrocyte encapsulator dialyzer used in preparing large quantities of erythrocyte ghosts and encapsulation of pesticide in erythrocyte ghosts. Analytical Biochemistry vol. 102 (1980) 220-227; Baker, R. F. Entry of ferritin into human red cells during hypotonic haemolysis. Nature vol. 215 (1967) 424-425; Marsden, N. V. B., and Ostling, S. G. Accumulation of dextran in human red cells after haemolysis. Nature vol. 184 (1959) 723-724]. In this approach, advantage is taken of the fact that mild osmotic hemolysis induces changes in the membrane porosity of the red cells which allows probes of approximately the same size as proteins and small solutes to partition into the interior of the red cells. By appropriately manipulating the ionic strength (restoration of isotonic conditions) after hemolysis, the pores can be resealed, trapping the partitioned solute permanently in the red cell (also known as erythrocyte ghosts). Washing the resealed ghosts removes excess solute from the external medium. Loading of fluorescently labeled dextran to give fluorescent erythrocyte ghosts using this approach has also been reported in literature [Doberstein, S. K. et al. Fluorescent erythrocyte ghosts as standards for quantitative flow cytometry. Cytometry vol. 20 (1995) 14-18].

The use of resealed ghosts in an assay, however, requires that the cell surface proteins and their orientation are unaffected by the ghost preparation and the solute loading process. Specifically the use of low ionic strength buffer or absence of magnesium ions in the buffer may lead to disaggregation of the molecular components and inside-out folding of the membrane, rendering the product unusable for the current purpose.

Alternate methods of fluorescently encoding cells include use of membrane permeable lipophilic dyes [Tanaka, Y. and Schroit, A. J. Insertion of fluorescent phosphatidylserine in the plasma membrane of red blood cells. J. Biol. Chem. vol. 258 (1983) 11335-11343; Tokumasu, F. and Dvorak, J. Development and application of quantum dots for immunochemistry of human erythrocytes. Journal of Microscopy, vol. 211 (2003) 256-261] and irreversible covalent linking of reactive dyes to the cell surface [Donald, M. M. et al. RBC's labeled at two biotin densities permit simultaneous and repeated measurements of circulating RBC volume. Transfusion, vol 44 (2004) 431-437; Suzuki, T. and Dale, G. L. Biotinylated erythrocytes: In-vivo survival and in vitro recovery. Blood, vol. 70 (1987) 791-795]. Little if any data exists about the effect of covalent attachment on ligand-receptor interactions [Cowley, H., et al. Biotinylation modifies red cell antigens. Transfusion, vol. 39 (1999) 163-168.]. In addition, large numbers of distinct codes are difficult to construct using the surface encoding approach, unless, where a few dyes are used to generate a number of different colors, the encoding reaction is closely regulated, or, a large library of dyes with different spectral fingerprints is used. Thus, an encoding method in which only few dye colors can be used, without close monitoring of the reaction is desired.

In a multiplexed assay format using encoded ghost cells and a secondary antibody to indicate binding of antibodies in the sample to the ghosts, decoding of an array of ghost cells can be done, e.g., with flow cytometry [Wagner, F. F. and Flegel, W. A. Principles and applications of red blood cell flow cytometry. Transfusion Medicine and Hemotherapy vol. 25 (1998); Roback, J. D., Barclay, S. and Hillyer, C. D. An automatable platform for accurate Immunohematology testing by flow cytometry. Transfusion Vol. 43 (2003) 918; Roback, J. D., Barclay, S. and Hillyer, C. D. Improved method for fluoresce cytometric immunohematology testing. Transfusion vol. 44 (2004) 187; Sharon, R. and Fibach, E. Quantitative flow cytometric Analysis of ABO Red Cell Antigens. Cytometry vol. 12 (1991) 545-549; Arndt, P. A. and Garratty, G. Flow cytofluorometric analysis in red blood cell immunology. Transfusion Medicine and Hemotherapy vol. 31 (2004)]. Other decoding methods, which allow for in-situ decoding with its concomitant advantages of higher throughput, are desirable.

SUMMARY

Disclosed are methods for detection and characterization of RBC alloantibodies, based on generating fluorescently encoded red blood cell or red blood cell ghosts, with known antigen presentation, and using them to detect the presence of antibody in a blood/serum/plasma sample, preferably using a fluorescence sandwich type immunoassay. Multiple populations of fluorescent RBC or RBC ghosts are first generated, wherein each population representing a particular phenotype is uniquely associated with a fluorescent signature or a code. In the case of a positive reaction, alloantibody in the sample binds to the cognate antigen on the encoded cells forming an antigen-antibody complex. Following a wash to remove unbound immunoglobins, a fluorescent secondary reagent (with a different spectral signature than the encoding dyes) is introduced, which binds to the alloantibodies captured on the cells. The assay signal generated by the fluorescent secondary reagent can be correlated with particular cells/ghosts, by correlating binding with the encoding fluorescence, to thereby identify the antigens presented on the cells and the cognate alloantibody. The decoding of the encoded cells can be done in-situ using fluorescence microscopy and 2-D image analysis, wherein a decoding image is compared and correlated with an assay image (see, e.g., allowed U.S. application Ser. No. 09/448,420).

DETAILED DESCRIPTION

The following examples outline the process of encoded ghost cell preparation, as well as performing an assay using the encoded ghost cells. The process permits encoding with only a few dyes, without requiring close monitoring of the reaction, and the resulting ghosts present antigens in the correct orientation so as to detect antibody in a sample, when used in a fluorescence-type immunoassay. Examples of in-situ decoding of the assay results are also included.

In preparing encoded ghost cells, the preferred buffer conditions (pH near neutral, approximately isotonic ionic strength for the buffer and Magnesium ions at a concentration of 0.1 to 2 mM) help preserve the reactivity and the native orientation of cell-surface proteins, and prevents them from being inverted so as to become inaccessible. An exemplary method is set forth in Example I below.

EXAMPLE 1

Red Cell Separation and Labeled Ghost Preparation

Figure 1A:
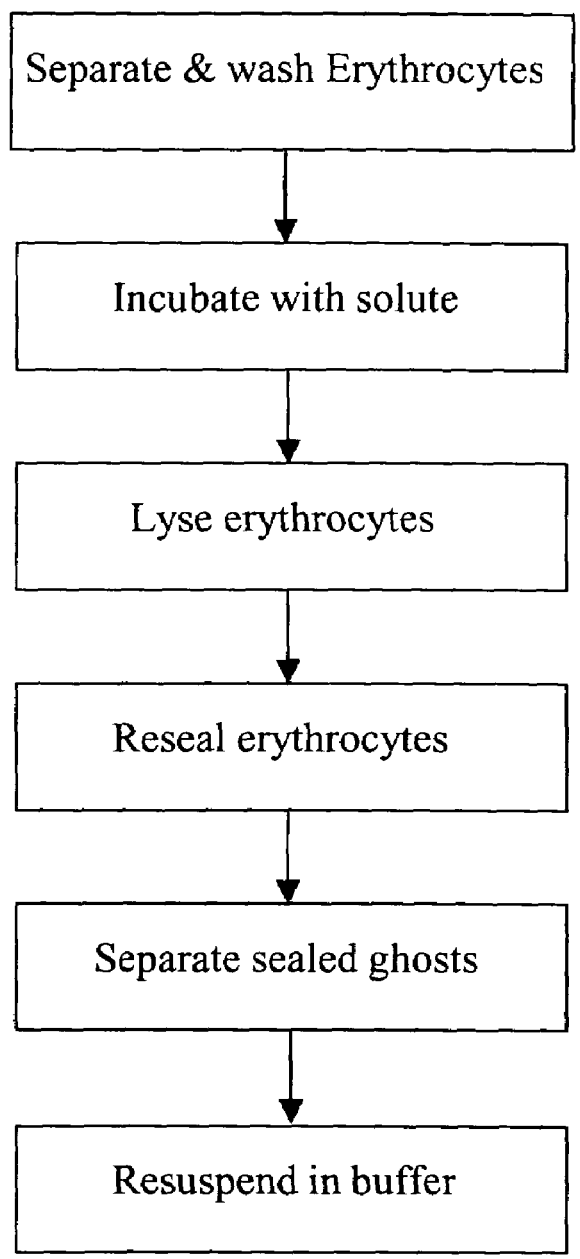
FIG. 1A is a flow chart for red blood cell separation and ghost cell preparation.
Figure 1B:
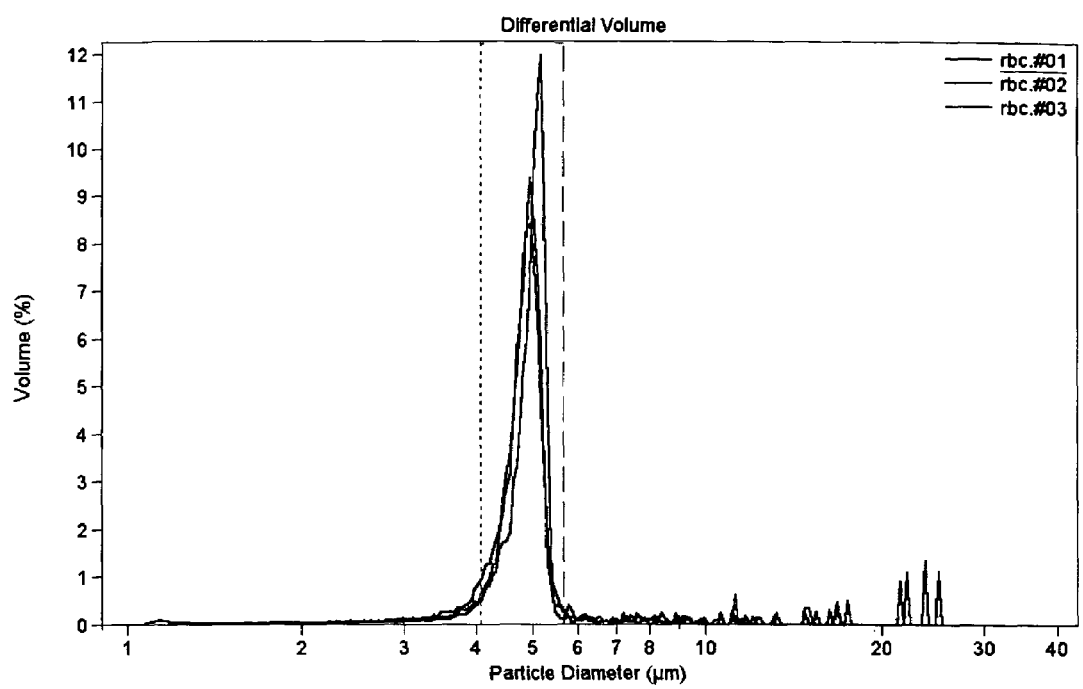
FIG. 1B shows the size distribution of the red blood cells and ghosts.
Figure 1C:
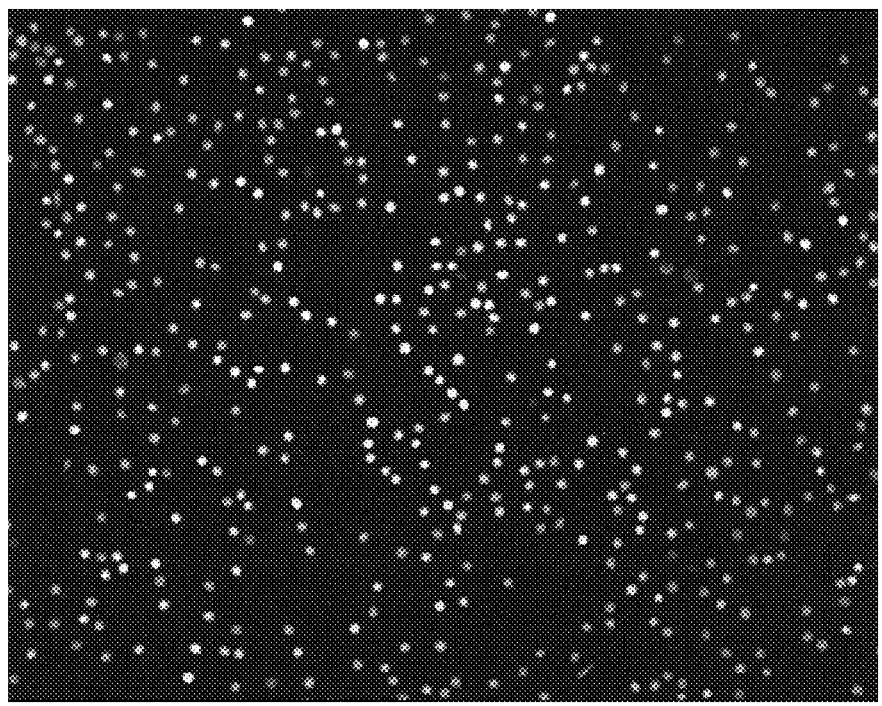
FIG. 1C the fluorescent image of the ghost cell encoded using the above process.

Red cell wash-storage buffer:
Sodium chloride=4.383 g
Monosodium Phosphate=0.345 g
Magnesium chloride hexahydrate=0.203 g
Phenylmethylsulfonylchloride=0.0435 g, dissolved in 500 ml of distilled water.
Red cell lysis buffer:
Monosodium Phosphate=0.69 g
Magnesium chloride hexahydrate=0.203 g
Phenylmethylsulfonylchloride=0.0435 g, dissolved in 500 ml of distilled water.
Red cell seal solution:
Sodium chloride=6 g, dissolved in 50 ml of distilled water Procedure:
i) Take 1 ml of the storage buffer in 2 ml centrifuge tube
ii) Add 1 drop of finger pricked fresh blood (~25 ul) and mix by gentle inversion
iii) Centrifuge at ~600-1000 g for 2 minutes, remove supernatant. Add 1.5 ml of storage buffer, gently re-suspend RBC pellet and repeat centrifugation. Discard supernatant, repeat 2×.

iv) Prepare desired concentration of fluorescent solute (or solute mixture) in storage buffer and add 200 ul of the solution to the red cell pellet. Incubate for 5 minutes at RT.
v) Add 1.5 ml of RBC lysis buffer to solution in (iv), mix quickly by inversion, incubate for 30 s at RT
vi) Add 250 ul of RBC seal solution to (v) and mix by inversion.
vii) Centrifuge at ~16,000 g for 3 min, discard supernatant. Resuspend ghost pellet in 1.5 ml storage buffer and repeat centrifugation-redispersal cycle 3×.
viii) Resuspend pellet in 1 ml of final storage buffer with 0.13 g/L sodium azide and store at 2-4° C. till used. The ghosts are stable as stored for more than a month.
FIG. 1(a) shows a flow chart of the process. FIG. 1(b) shows the size distribution and FIG. 1(c) the fluorescent image of the ghost cell encoded using the above process.

EXAMPLE 2

Generation of a Library of Encoded Ghost Cells

Figure 2A:
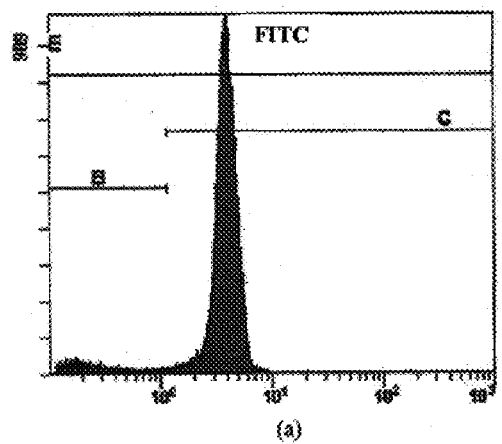
FIG. 2A shows fluorescence intensity vs. concentration for FITC-dyed ghosts.
Figure 2B:
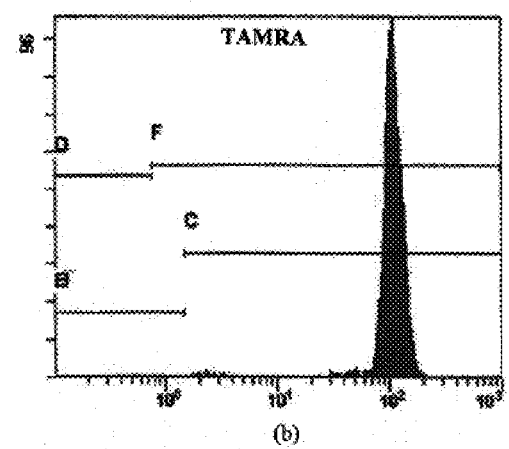
FIG. 2B shows fluorescence intensity vs. concentration for TAMRA-dyed ghosts.
Figure 2C:
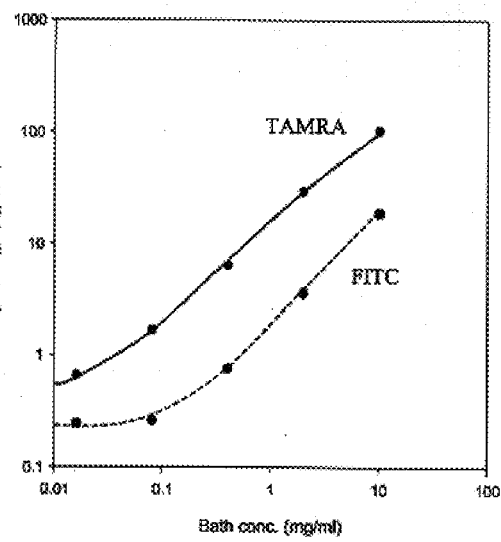
FIG. 2C shows the plot of fluorescence intensity vs. concentration of FIGS. 2A and 2B.

TAMRA labeled dextran of molecular weight 3000 (labeling density 1 mol/mol) was obtained from Molecular Probes and FITC-labeled dextran of molecular weight 4000 (labeling density 0.05 mol/mol-0.5/mol/mol) was obtained from Sigma-Aldrich. Five different stock solutions of concentrations 10 mg/ml, 2 mg/ml, 0.4 mg/ml, 0.08 mg/ml and 0.016 mg/ml were prepared from each using the storage buffer. 10 different populations of encoded ghosts were prepared using the recipe described in example 1. The ghosts were characterized for their fluorescence using flow cytometry and the results are shown in FIG. 2. FIGS. 2(a) and (b) show fluorescent intensity histograms of FITC and TAMRA containing ghosts.

Separately 1:1 (v/v) mixtures of the TAMRA and FITC dextran were used to generate encoded ghosts carrying two encoding dyes.

EXAMPLE 3

Generation of a Library of Magnetically Responsive Encoded Ghost Cells

The encoded ghost cells can be rendered magnetic by magnetic cell surface labeling methods known in art. Several companies sell kits for magnetically labeling and isolating cell of interest (see the websites for Miltenyi Bbiotech, Immunicom and Dynal Biotech). Magnetically labeled whole blood cells are also available as a commercial product (see the website for Diagast Diagnostics). A particularly desired approach utilizes labeling with magnetic nanobeads coated with anti-human IgG, which can be added following the binding of antibody from the sample, as outlined in FIG. 2.

EXAMPLE 4

Methods of Decoding Encoded Ghosts

The methods outlined above generate fluorescently encoded ghosts that are bright, photostable and easily multiplexed. A successful decoding strategy thus involves any platform that can achieve discrimination of a single cell population from within a mixed one, including conventional serial interrogation techniques like flow cytometry, which has been conventionally used to characterize red blood cells. Alternatively, fluorescent microscopy coupled with 2-D image analysis [designated READ™ see U.S. Pat. No. 6,797,524; see also "Array Cytometry" U.S. Pat. No. 6,387,707, both incorporated by reference] may be used for decoding. A variety of methods have been reported for creating 2-D array of cells including methods allowing pre-forming such as, spotting on functionalized substrates [Albrecht, D. R. et al. Photo-and electropatterning of hydrogel-encapsulated living cell arrays. Lab Chip vol. 5 (2005) 111-118; Soen, Y. et al. Detection and characterization of cellular immune responses using peptide-MHC microarrays. PLOS Biology vol. 1 (2003) 429-438; Kato, K. et al. Immobilized culture of nonadherent cells on an oleyl poly(ethylene glycol)ether-modified surface. Biotechniques vol. 35 (2003) 1014-1021], and entrapment on imaging fiber [Biran, I. And Walt, D. R. Optical imaging fiber-based single live cell arrays: A high-density cell assay platform. Analytical Chemistry vol. 74 (2002) 3046-3054]. In addition dynamic or real-time array assembly methods such as magnetic cell selection [Tibbe, A. G. J. et al. Cell analysis system based on immunomagnetic cell selection and alignment followed by immunofluorescent analysis using compact disk technologies. Cytometry vol. 43 (2001) 31-37], microfluidic channels [Shelby, J. P. et al. A microfluidic model for single-cell capillary obstruction by *plasmodium falciparum*-infected erythrocytes. Proc. Nat. Acad. Sci. vol. 100 (2003) 14618-14622] and AC electrophoresis [U.S. Pat. No. 6,387,707; Minerick, A. R. Manipulating and characterization of red blood cells with alternating current field in microdevices. Electrophoresis vol. 24 (2003) 3703-3717].

Figure 4:
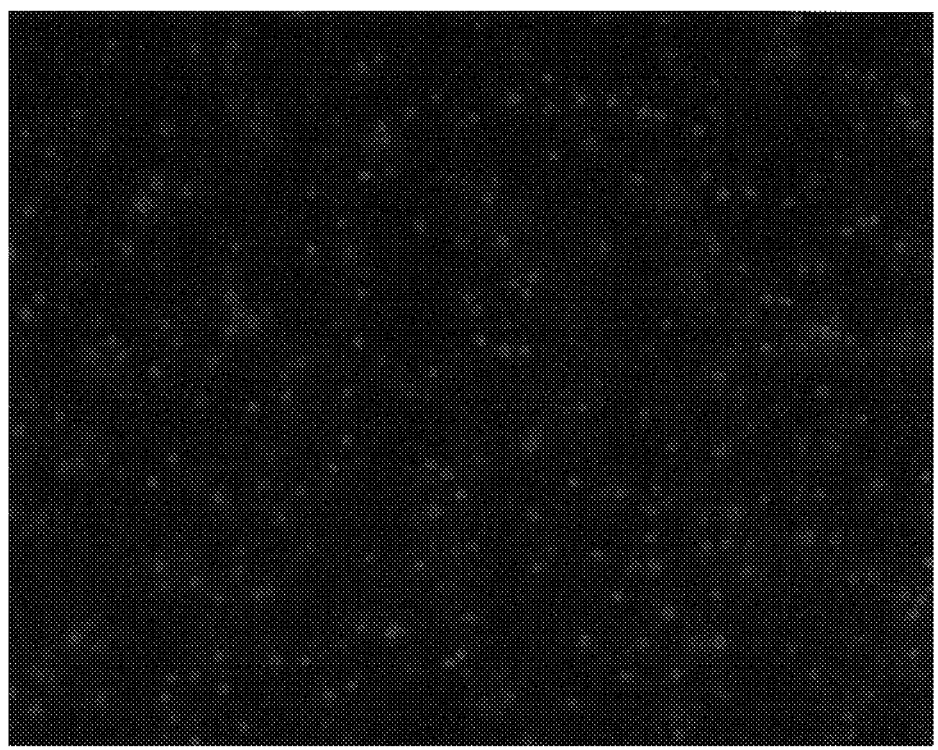
FIG. 4 shows a false color image depicting a random two-dimensional assembly of encoded ghost cells.
Figure 5:
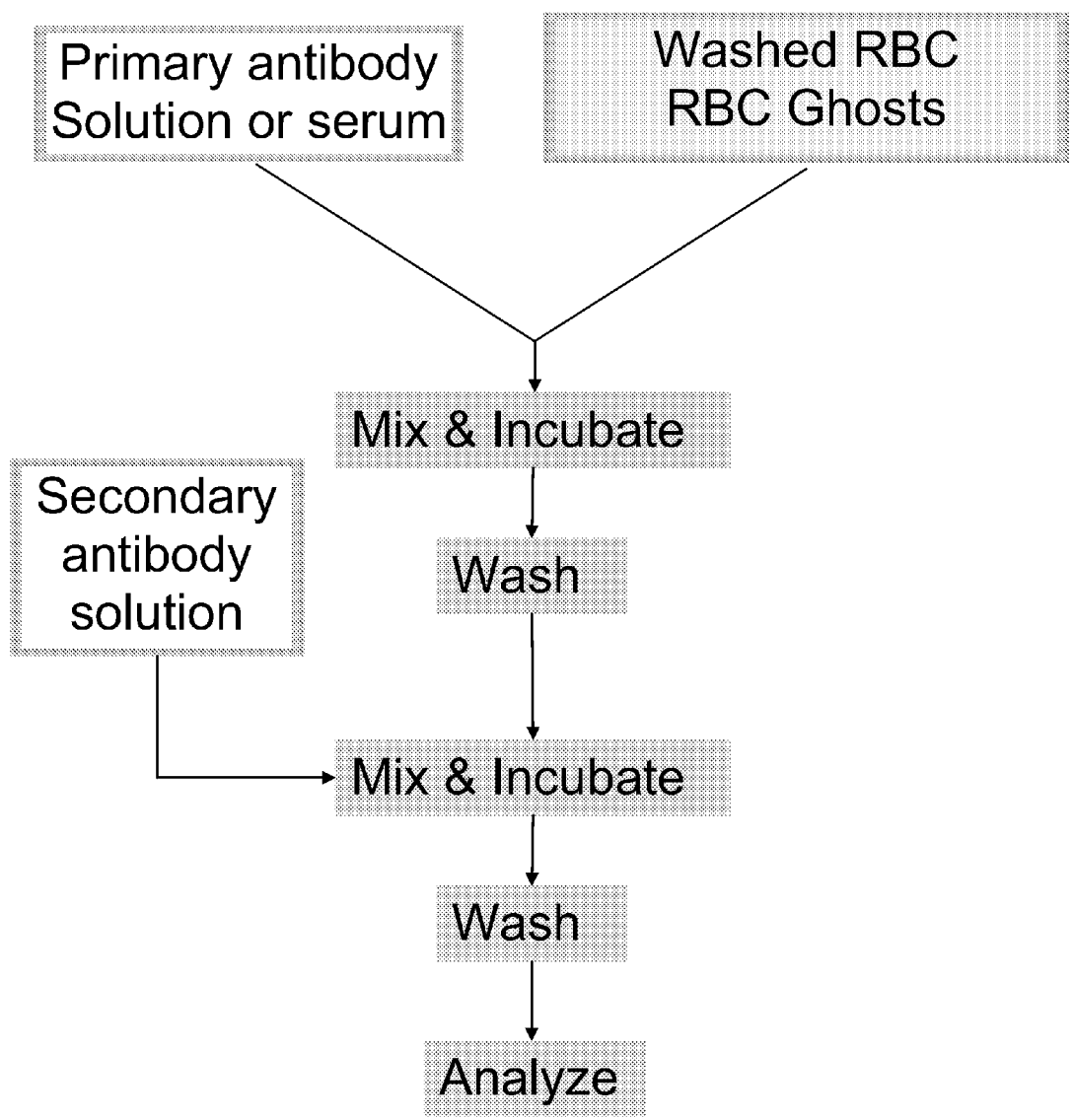
FIG. 5 is a flow chart of a procedure for detecting reactive antibodies in sera using ghosts and a secondary detection antibody in a sandwich assay format.
Figure 6A:
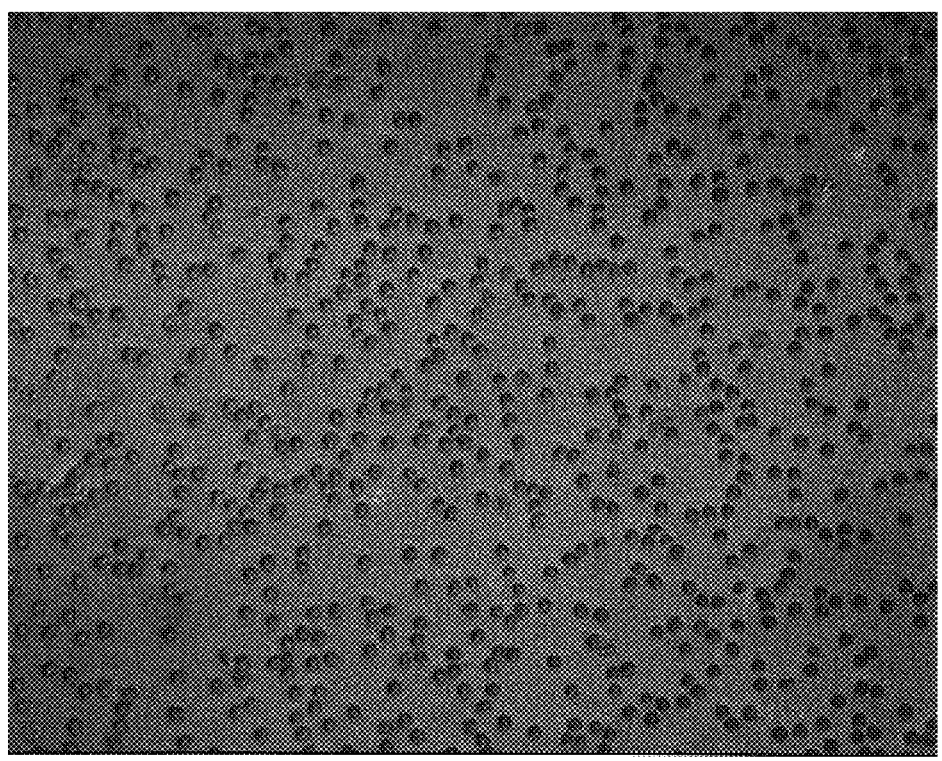
FIGS. 6A and 6B shows the images of whole RBC cells after completion of an immunoassay with monoclonal antibodies targeting cell surface antigens.
Figure 6B:
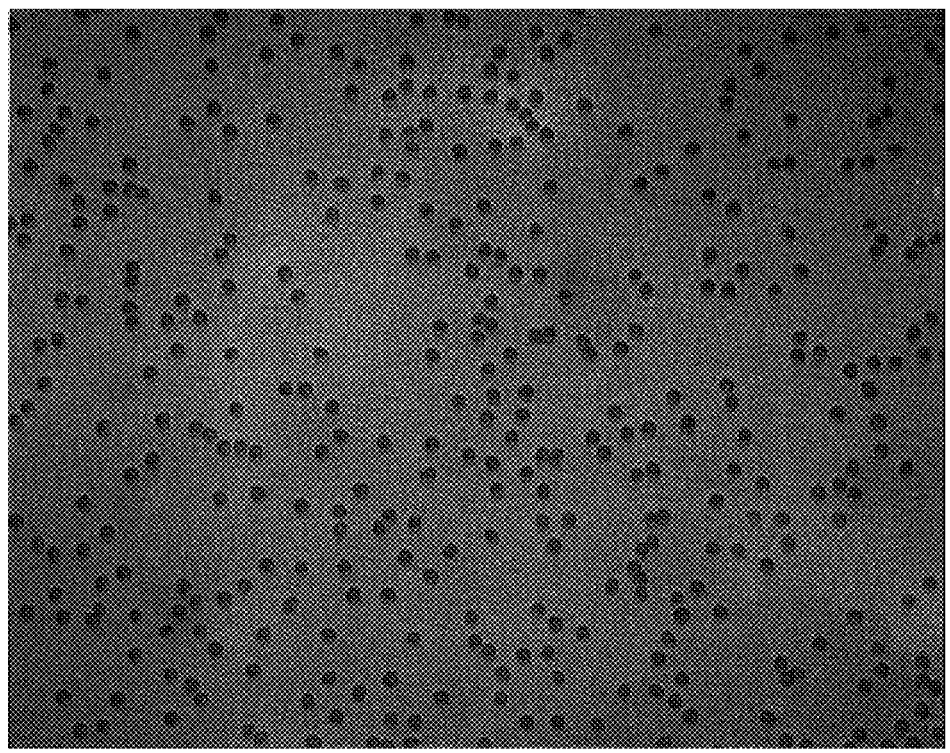

FIG. 4 shows a false color image of a random two-dimensional assembly of encoded ghost cells (5 types in total: two levels of red, two levels of blue and one level of red/blue or purple)

EXAMPLE 5

Immunoassay using Whole Red Cells

Figure 3:
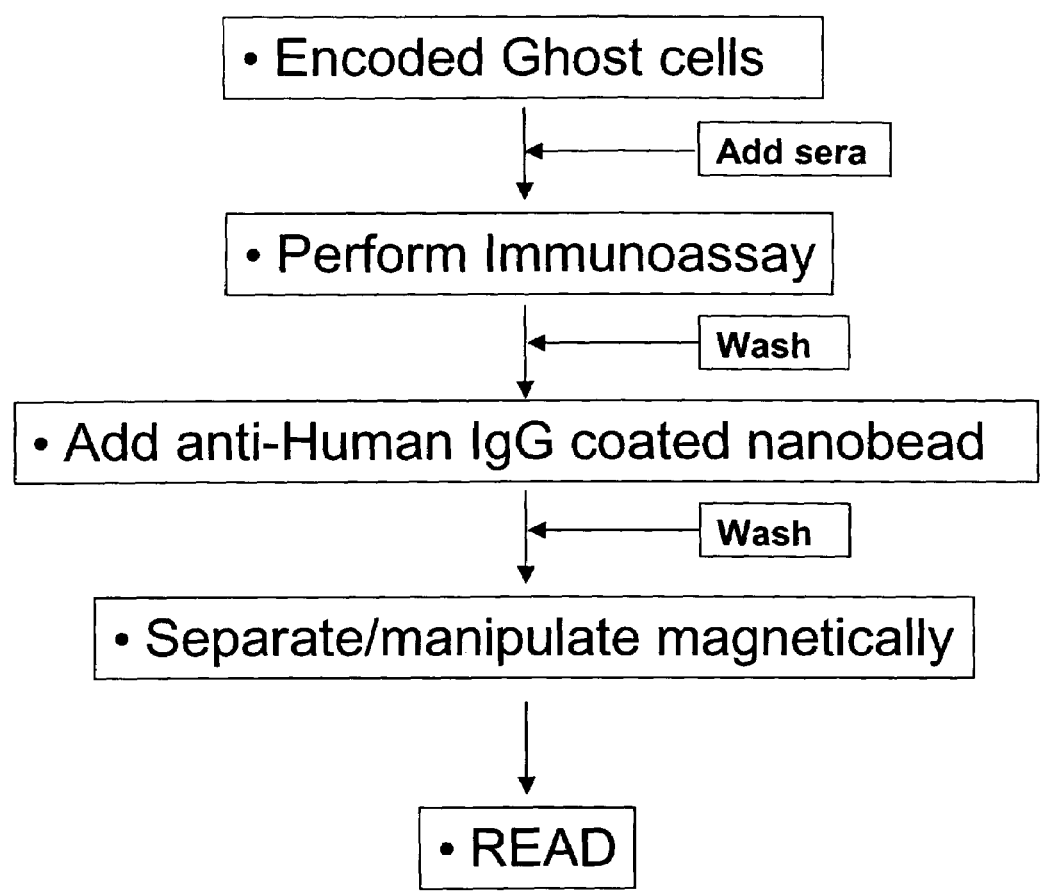
FIG. 3 is a flow chart for an exemplary procedure wherein following binding, magnetic beads displaying secondary antibody on their surface are used to capture the reactive ghosts in an array for decoding.

FIG. 3 shows a process-flow for performing an immunoassay using whole blood or RBC ghosts. In this example washed whole RBC (Phenotype Fy(a+, b−), (K−, k+)) was separately reacted with Monoclonal Murine anti-Fy$^a$ and Monoclonal Murine anti-K (both a gift from the lab of Dr. Marion Reed, New York Blood Center). In both the cases, Cy5-labeled goat anti-mouse polyclonal antibody (Jackson Immunoresearch, West Grove, Pa.) was used as the secondary fluorescent detection antibody. As expected, specific signal is seen in the case of anti-Fy$^a$ and not in case of anti-K antibody (results not shown).

EXAMPLE 6

Immunoassay using Encoded Ghosts

Figure 7:
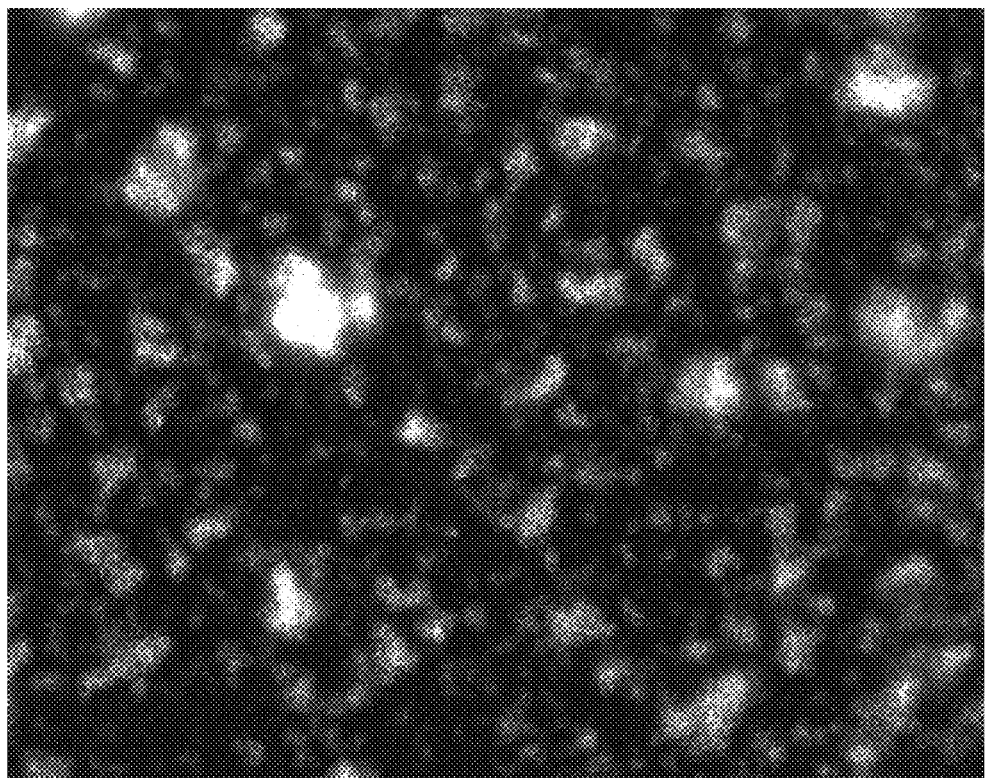
FIG. 7 shows the image of RBC ghost cells after completion of an immunoassay using an anti-M antibody (which the ghosts were positive for).

An immunoassay was performed using ghost cells prepared from washed whole RBC (Phenotype (M+, N−)) and Monoclonal Murine anti-M and anti-N antibody (US Biological, Swampscott, Mass.), as outlined in Example 5. Reaction with anti-M produced the expected fluorescent signal, whereas, as expected, anti-N did not produce any detectable signal over background. FIG. 7 shows the image of the RBC ghosts after completion of the immunoassay using anti-M antibody.

It should be understood that the terms, expressions and examples herein are exemplary only and not limiting, and that the scope of the invention is limited only by the claims which follow, and includes all equivalents of the claimed subject matter.

What is claimed is:

1. A method for detecting and identifying alloantibodies in a blood sample, comprising:

generating a set of several differently encoded red blood cells or red blood cell ghosts displaying antigens on the cell surface whose identities are known, such that differently encoded red blood cells or red blood cell ghosts in the set are antigenically distinct from other red blood cells or red blood cell ghosts in the set;

wherein said differently encoded cells or ghosts contain two or more fluorescent dyes mixed at different predetermined ratios which upon excitation exhibit distinct fluorescent emission signals, wherein the ratio of the fluorescent emission signals is governed by said predetermined ratio and wherein the presence of the fluorescent dye does not substantially alter the antigenicity of the cells or ghosts;

contacting said set with said blood sample under conditions permitting binding of said alloantibodies present in the sample to the antigens on the cell surface;

removing the excess blood sample components from contact with the set thereby leaving alloantibody bound to the antigens on the cell surface;

detecting the presence of the bound alloantibody on red blood cells or red blood cell ghosts using a labeled secondary antibody that binds to alloantibodies captured by the red blood cells or red blood cell ghosts by determining the presence of signals from the labeled secondary antibody;

determining the ratio of fluorescent encoding signals associated with different red blood cells or red blood cell ghosts; and correlating the signals from the labeled secondary antibody with the ratio of fluorescent encoding signal for red blood cells or red blood cell ghosts; and determining the identity of the alloantibody.

2. The method of claim 1 wherein the secondary antibody is labeled with a fluorescent dye.

3. The method of claim 1 wherein the secondary antibody is monoclonal.

4. The method of claim 1 wherein the detecting step is performed with flow cytometry or by imaging an array of the encoded cells or ghosts, imaging the bound secondary antibodies and correlating the position of the labeled secondary antibodies that bound with the array image to determine which cells or ghosts in the set bound to alloantibodies in the sample.

5. The method of claim 1 wherein the blood sample is serum blood or plasma.

* * * * *